United States Patent
Xu et al.

(10) Patent No.: US 10,889,606 B2
(45) Date of Patent: Jan. 12, 2021

(54) BIFLAVONE-IRON COMPLEX, PREPARATION METHOD AND APPLICATION THEREOF

(71) Applicant: NANJING FORESTRY UNIVERSITY, Nanjing (CN)

(72) Inventors: Li Xu, Nanjing (CN); Fuliang Cao, Nanjing (CN); Shilong Yang, Nanjing (CN)

(73) Assignee: NANJING FORESTRY UNIVERSITY, Nanjing (CN)

( * ) Notice: Subject to any disclaimer, the term of this patent is extended or adjusted under 35 U.S.C. 154(b) by 22 days.

(21) Appl. No.: 16/487,848

(22) PCT Filed: Feb. 13, 2018

(86) PCT No.: PCT/CN2018/076732
§ 371 (c)(1),
(2) Date: Aug. 22, 2019

(87) PCT Pub. No.: WO2018/153328
PCT Pub. Date: Aug. 30, 2018

(65) Prior Publication Data
US 2020/0239506 A1    Jul. 30, 2020

(30) Foreign Application Priority Data
Feb. 22, 2017 (CN) .......................... 2017 1 0097598

(51) Int. Cl.
A61P 39/06    (2006.01)
C07F 15/02    (2006.01)

(52) U.S. Cl.
CPC ............ *C07F 15/025* (2013.01); *A61P 39/06* (2018.01)

(58) Field of Classification Search
None
See application file for complete search history.

(56) References Cited

FOREIGN PATENT DOCUMENTS

| CN | 101857583 A | 10/2010 |
| CN | 101891783 A | 11/2010 |
| CN | 106749344 A | 5/2017 |
| CN | 106883273 A | 6/2017 |
| CN | 106892946 A | 6/2017 |
| CN | 106905353 A | 6/2017 |
| CN | 106905371 A | 6/2017 |

OTHER PUBLICATIONS

Lee. E, et al. Cytotoxic Activities of Amentoflavone Against Human Breast and Cervical Cancers are Mediated by Increasing of PTEN Expression Levels Due to Peroxisome Proliferator-Activated RecptorY Actiation. Bulletin of the Korean Chemical Society, 2012, 33(7), pp. 2219-2223.
Chen J. H. et al. Amentoflavone Induces Anti-Angiogenic and Anti-Metastatic Effects Through Suppression of NF-Kappa B Activation in MCF-7 Cells. Anticancer Research, 2015, 35(12):6685-6694.
Lee C. W. et al. Amentoflavone Inhibits UVB-Induced Matrix Metalloproteinase-1 Expression Through the Modulation of AP-1 Znmponents in Normal Human Fibroblasts. Applied Biochemistry and Biotechnology 2012, 166, pp. 1137-1147.
Zhang Y.P. et al. Target-Guided Isolation and Purification of Antioxidants from Selaginella Sinensis by Offline Znupling of DPPH-HPLC and HSCCC Experiments. Journal of Chromatography B, 2011, 879, pp. 191-196.
Li X.C., et al. Amentoflavone Protects against Hydroxyl Radical-Induced DNA Damage via Antioxidant Mechanism. Turkish Journal of Biochemistry—Turk Biyokimya Dergisi, 2014, 39(1), pp. 30-36.
Zhou J., et al. Synthesis, Characterization, Antioxidative and Antitumor Activities of Solid Quercertin Rare Earth(III) Complexes. Journal of Inorganic Biochemistry, 2001, 83, pp. 41-48.
Cao Zhiquan, New Thinking About Study of Pharmacodynamic Material and Functional Mechanism in Chinese Materia Medica—Study on the Relation between Morphology and Biological Activity of Chemical Species in Chinese Materia Medica, Acta Universitatis Traditionis Medicalis Sinensis Pharmacologiaeque Shanghai, Mar. 2000, vol. 14, No. 1, pp. 36-40.
Selvaraj, S. et al. Flavonoid-Metal Ion Complexes: A Novel Class of Therapeutic Agents, Medicinal Research Reviews, 34(4), 29, Aug. 2013, pp. 677-702.
Kasprzak, M. M. et al. Properties and Applications of Flavonoid Metal Complexes, RSC Adv., 5(57), May 12, 2015, pp. 45853-45877.
Uddin, Q. et al. The Biflavonoid, Amentoflavone Degrades DNA in the Presence of Copper Ions, Toxicology in Vitro, Aug. 31, 2004, vol. 18, pp. 435-440.

*Primary Examiner* — Alton N Pryor
(74) *Attorney, Agent, or Firm* — Bayramoglu Law Offices LLC

(57) ABSTRACT

A method for preparing a biflavone-iron complex, includes using the amentoflavone as the ligand and the ferric ion as the central ion, the amentoflavone-iron complex is obtained by reaction, and the structure of the complex is characterized by infrared spectroscopy, UV-vis absorption spectroscopy and high resolution mass spectrometry. Meanwhile, the antitumor and antioxidant activities of the amentoflavone-iron complex are studied in the present invention. MTT method shows that the amentoflavone-iron complex has a relatively good antitumor activity, and the antitumor activity thereof is stronger than that of the amentoflavone. Pyrogallol auto-oxidation method and ABTS method show that the antioxidative activity of the amentoflavone-iron complex is stronger than that of the amentoflavone itself.

6 Claims, 9 Drawing Sheets

BIFLAVONE-IRON COMPLEX, PREPARATION METHOD AND APPLICATION THEREOF

CROSS REFERENCE TO THE RELATED APPLICATIONS

This application is the national phase entry of International Application No. PCT/CN2018/076732, filed on Feb. 13, 2018, which is based upon and claims priority to Chinese Patent Application No. 201710097598.4, filed on Feb. 22, 2017, the entire contents of which are incorporated herein by reference.

TECHNICAL FIELD

The present invention belongs to the technical fields of organic synthesis and medicine, specifically relating to a biflavone-iron complex, a preparation method and an application thereof.

BACKGROUND

Biflavonoid compounds are unique chemical components of gymnosperms such as ginkgo, Selaginella tamariscina, etc., which have biological activities such as anti-oxidation, anti-inflammatory, anti-viral, antitumor and the like. Among them, amentoflavone (Ame) is a relatively more common one of the biflavonoid compounds with a structural formula shown as follows.

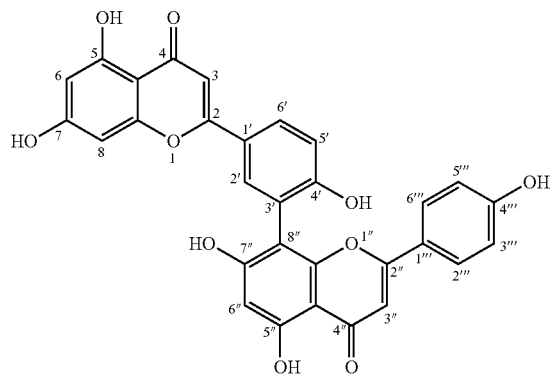

Sun et al. has researched and found that the amentoflavone can increase the expression of anti-cancer genes by activating hPPARγ, thereby achieving the effect of inhibiting breast cancer cells and cervical cancer cells (Lee E., Shin S., Lee J. et al. Cytotoxic activities of amentoflavone against human breast and cervical cancers are mediated by increasing of PTEN expression levels due to peroxisome proliferator-activated receptor γ activation [J]. Bulletin of the Korean Chemical Society, 2012, 33 (7): 2219-2223.). Chen et al. has researched and found that the amentoflavone blocks the formation of blood vessels and the metabolism of cancer cells through inhibiting the activity of factor NF-kappa B, achieving the purpose of inhibiting the growth of tumor cells (Chen J. H., Chen W. L., Liu Y. C. Amentoflavone induces anti-angiogenic and anti-metastatic effects through suppression of NF-kappa B activation in MCF-7 cells [J]. Anticancer Research, 2015, 35 (12):6685-6693.). Lee et al. has researched and found that the amentoflavone may inhibit UVB-induced matrix metalloproteinase expression, thereby exerting anti-oxidation and anti-radiation effects (Lee C. W., Na Y., Park N., et al. Amentoflavone inhibits UVB-induced matrix metalloproteinase-1 expression through the modulation of AP-1 Femponents in normal human fibroblasts [J]. Applied Biochemistry and Biotechnology, 2012, 166:1137-1147.). Zhang et al. has researched and found that the amentoflavone and ginkgetin have certain antioxidant activity and strong ability to scavenge DPPH free radicals (Zhang Y. P., Shi S. Y., Wang Y. X., et al. Target-guided isolation and purification of antioxidants from Selaginella sinensis by offline Feupling of DPPH-HPLC and HSCCC experiments [J]. Journal of Chromatography B, 2011, 879: 191-196.). Li et al. has researched and showed that the amentoflavone has an antioxidant activity, which may effectively scavenge free radicals such as $OH^-\cdot$, $O^{2-}\cdot$, DPPH$\cdot$, ABTS$^+\cdot$, etc., and protect DNA from oxidative damage caused by $OH^-\cdot$. (Li X. C., Wang L., Han W. J., et al. Amentoflavone protects against hydroxyl radical-induced DNA damage via antioxidant mechanism [J]. Turkish Journal of Biochemistry-Turk Biyokimya Dergisi, 2014, 39 (1): 30-36.).

The coordination chemistry of traditional Chinese medicines shows that complex equilibria exists in the complexes formed by the reaction between trace elements and organic compounds, so the biological activities of the original components can be exhibited. Moreover, since the synergy and antagonism that exists in trace elements, organic components, complexes and a combination thereof may weaken or enhance the biological activities of the original components, new biological activities may also be generated (Cao Zhiquan. New thoughts of studying material basis and mechanism of the efficacy of traditional Chinese medicine (1)-Study on the relationship between the speciation and biological activity of chemical species in traditional Chinese medicine [J]. Journal of Shanghai University of Traditional Chinese Medicine, 2000, 14 (1): 36-39.). For example, Zhou et al. has researched and found that the quercetin rare earth complex has higher ability to scavenge $O_2^-\cdot$ than the quercetin. The quercetin rare earth complex can inhibit a variety of tumors, and antitumor activity thereof is higher than that of the quercetin. Specifically, the complex has a higher inhibitory effect on bladder tumor cells, while the quercetin does not have such effect (Zhou J., Wang L. F., Wang J. Y., et al. Synthesis, characterization, antioxidative and antitumor activities of solid quercetin rare earth(III) complexes [J]. Journal of Inorganic Biochemistry, 2001, 83: 41-48.).

However, to date, studies on the synthesis of the biflavone complex and the biological activity thereof have not been reported.

SUMMARY

Objectives of the Present Invention: In view of the deficiencies in the prior art, one objective of the present invention is to provide an amentoflavone-iron complex, which meets the application needs of antitumor and antioxidation drugs. Another objective of the present invention is to provide a preparation method of the above-mentioned biflavone-iron complex. A further objective of the present invention is to provide an application of the biflavone-iron complex.

Technical Solution: In order to achieve the above objectives, the technical solution of the present invention is as follows.

The biflavone-iron complex has the following structural formula:

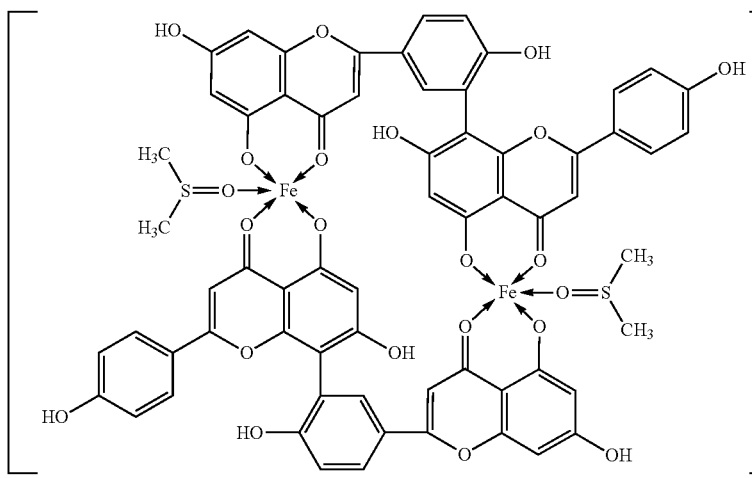

X is $NO_3^-$ or $Cl^-$.

A method of preparing a biflavone-iron complex is as follows: dissolving a ferric salt in an alcohol and then adding into a biflavone dissolved in an alcohol; performing a reaction for 2-5 h to form a precipitate at a pH controlled to 5-7 and under heating and stirring; filtering the precipitate, washing with alcohol and water, recrystallizing using dimethyl sulfoxide as a solvent, and drying to obtain the biflavone-iron complex.

The biflavone is an amentoflavone, but is not limited to the amentoflavone, and generally refers to biflavonoid compounds having 5-OH and 4-C=O, or having 5"-OH and 4"-C=O.

The ferric salt is an alcohol-soluble ferric salt such as ferric nitrate, ferric chloride, etc.

The solvent is ethanol, methanol and methanol/ethanol aqueous solution of various concentrations, etc.

The pH is adjusted with an alkali alcohol solution, and the alkali used in the alkali alcohol solution includes common bases such as sodium hydroxide, potassium hydroxide, aqueous ammonia, sodium ethoxide, sodium methoxide, etc.

During the reaction, the heating temperature is 30° C.-50° C., and the reaction time is 2-5 h. The molar ratio of the biflavone to ferric ion in the solution is 2-2.5:1.

The solvent used in the recrystallization is dimethyl sulfoxide, and the drying method is freeze-drying, low temperature vacuum-drying, etc.

The biflavone-iron complex is used in a preparation of an antitumor drug and/or an antioxidant drug.

Advantages: compared with the prior art, the amentoflavone-iron complex is first synthesized in the present invention. The antitumor activity of the Ame-Fe complex is studied by the MTT method, and the results show that the ability of the Ame-Fe complex to inhibit hepatoma cells (HepG2) and cervical cancer cells (HeLa) is stronger than that of the Ame itself. Through UV-vis absorption spectroscopy, fluorescence spectroscopy and viscosity methods, it shows that the mechanism of antitumor activity of the Ame-Fe complex may be that the complex is inserted into DNA in an intercalation manner, causing apoptosis. Through the pyrogallol auto-oxidation method and ABTS method, it shows that the Ame-Fe complex has stronger ability to scavenge free radicals than the Ame itself, indicating that the antioxidant activity of the complex is stronger than that of Ame, which is conducive to the further development of the biflavonoid compounds, provides a basis for the research of new drugs, and contributes to the development of human health.

DETAILED DESCRIPTION OF THE EMBODIMENTS

Figure 1:
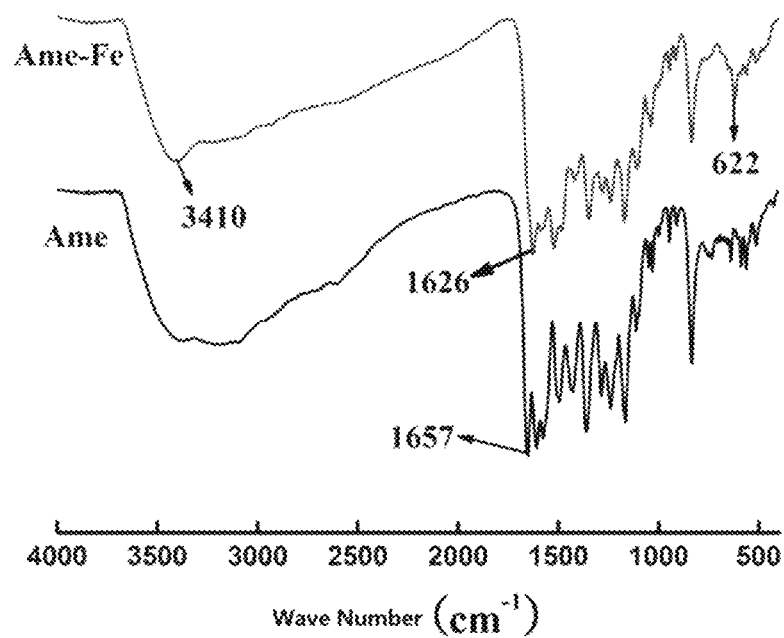
FIG. 1 is a diagram showing IR spectra of an Ame and an Ame-Fe complex.

The present invention will be further described below in conjunction with specific embodiments.

Embodiment 1

53.8 mg of Ame was accurately weighed and put in a round bottom flask, then the Ame was dissolved with 5 mL of ethanol; 20.2 mg of ferric nitrate nonahydrate was precisely weighed and dissolved with 5 mL of ethanol; the ferric nitrate solution was dropwise added to the Ame solution, ethanol-ammonia water (V/V, 3:1) solution was dropwise added to the reaction solution to adjust the pH to 6, and the reaction was performed at 30° C. for 4-5 h to obtain a precipitate; the precipitate was filtered, successively washed with ethanol and water, recrystallized with DMSO, and freeze-dried to obtain the Ame-Fe complex.

Embodiment 2

53.8 mg of Ame was accurately weighed and put in a round bottom flask, then the Ame was dissolved with 5 mL of 90% ethanol; 20.2 mg of ferric nitrate nonahydrate was precisely weighed and dissolved with 5 mL of 90% ethanol; the ferric nitrate solution was dropwise added to the Ame solution, ethanol-sodium ethoxide solution was dropwise added to the reaction solution to adjust the pH to 5, and the reaction was performed at 30° C. for 4-5 h to obtain a precipitate; the precipitate was filtered, successively washed with ethanol and water, recrystallized with DMSO, and freeze-dried to obtain the Ame-Fe complex.

Embodiment 3

53.8 mg of Ame was accurately weighed and put in a round bottom flask, then the Ame was dissolved with 5 mL of methanol; 20.2 mg of ferric nitrate nonahydrate was precisely weighed and dissolved with 5 mL of methanol; the ferric nitrate solution was dropwise added to the Ame solution, methanol-sodium methoxide solution was dropwise added to the reaction solution to adjust the pH to 7, and the reaction was performed at 40° C. for 3-4 h to obtain a precipitate; the precipitate was filtered, successively washed with methanol and water, recrystallized with DMSO, and freeze-dried to obtain the Ame-Fe complex.

Embodiment 4

53.8 mg of Ame was accurately weighed and put in a round bottom flask, then the Ame was dissolved with 5 mL of 85% methanol; 20.2 mg of ferric nitrate nonahydrate was precisely weighed and dissolved with 5 mL of 85% methanol; the ferric nitrate solution was dropwise added to the Ame solution, methanol-sodium methoxide solution was dropwise added to the reaction solution to adjust the pH to 7, and the reaction was performed at 50° C. for 2-3 h to obtain a precipitate; the precipitate was filtered, successively washed with methanol and water, recrystallized with DMSO, and freeze-dried to obtain the Ame-Fe complex.

Embodiment 5

53.8 mg of Ame was accurately weighed and put in a round bottom flask, then the Ame was dissolved with 5 mL of ethanol; 13.5 mg of ferric chloride hexahydrate was precisely weighed and dissolved with 5 mL of ethanol; the ferric chloride solution was dropwise added to the Ame solution, ethanol-ammonia water (V/V, 3:1) solution was dropwise added to the reaction solution to adjust the pH to 6, and the reaction was performed at 30° C. for 4-5 h to obtain a precipitate; the precipitate was filtered, successively washed with ethanol and water, recrystallized with DMSO, and freeze-dried to obtain the Ame-Fe complex.

Embodiment 6

53.8 mg of Ame was accurately weighed and put in a round bottom flask, then the Ame was dissolved with 5 mL of 90% ethanol; 13.5 mg of ferric chloride hexahydrate was precisely weighed and dissolved with 5 mL of 90% ethanol; the ferric chloride solution was dropwise added to the Ame solution, ethanol-sodium ethoxide solution was dropwise added to the reaction solution to adjust the pH to 5, and the reaction was performed at 30° C. for 4-5 h to obtain a precipitate; the precipitate was filtered, successively washed with ethanol and water, recrystallized with DMSO, and freeze-dried to obtain the Ame-Fe complex.

Embodiment 7

53.8 mg of Ame was accurately weighed and put in a round bottom flask, then the Ame was dissolved with 5 mL of methanol; 13.5 mg of ferric chloride hexahydrate was precisely weighed and dissolved with 5 mL of methanol; the ferric chloride solution was dropwise added to the Ame solution, methanol-sodium methoxide solution was dropwise added to the reaction solution to adjust the pH to 7, and the reaction was performed at 40° C. for 3-4 h to obtain a precipitate; the precipitate was filtered, successively washed with methanol and water, recrystallized with DMSO, and freeze-dried to obtain the Ame-Fe complex.

Embodiment 8

53.8 mg of Ame was accurately weighed and put in a round bottom flask, then the Ame was dissolved with 5 mL of 85% methanol; 13.5 mg of ferric chloride hexahydrate was precisely weighed and dissolved with 5 mL of 85% methanol; the ferric chloride solution was dropwise added to the Ame solution, methanol-sodium methoxide solution was dropwise added to the reaction solution to adjust the pH to 7, and the reaction was performed at 50° C. for 2-3 h to obtain a precipitate; the precipitate was filtered, successively washed with methanol and water, recrystallized with DMSO, and freeze-dried to obtain the Ame-Fe complex.

Embodiment 9

The products prepared in Embodiments 1-8 were characterized. The IR spectra of the Ame and the Ame-Fe complex are shown in FIG. 1. As can be seen from the figure, the Ame has a broad absorption at 2800-3500 $cm^{-1}$, which is the stretching vibration peak of the associated hydroxyl group, because intramolecular hydrogen bonds are formed between 5-OH and 4-C=O, and between 5"-OH and 4"-C=O in the Ame molecule. However, in the Ame-Fe complex, the absorption is narrowed here, and the peak shape at about 3410 $cm^{-1}$ becomes sharp, indicating that the intramolecular hydrogen bond is destroyed after the formation of the complex. The strong peak at 1657 $cm^{-1}$ in the Ame is caused by the stretching vibration of the carbonyl group, which is the characteristic absorption peak of the carbonyl group.

After the complex is formed, the absorption peak moves toward the low wave number and moves to 1526 cm$^{-1}$, indicating that the carbonyl group participates in the coordination. The complex produces an absorption peak at 622 cm$^{-1}$, which is caused by the stretching vibration of Fe—O, effectively proving that oxygen atoms participate in the coordination. Therefore, it can be speculated that the carbonyl group and the hydroxyl group in the Ame participate in the coordination, and the most probable coordination sites are 5-OH, 4-C=O, 5″-OH and 4″-C=O.

Figure 2:
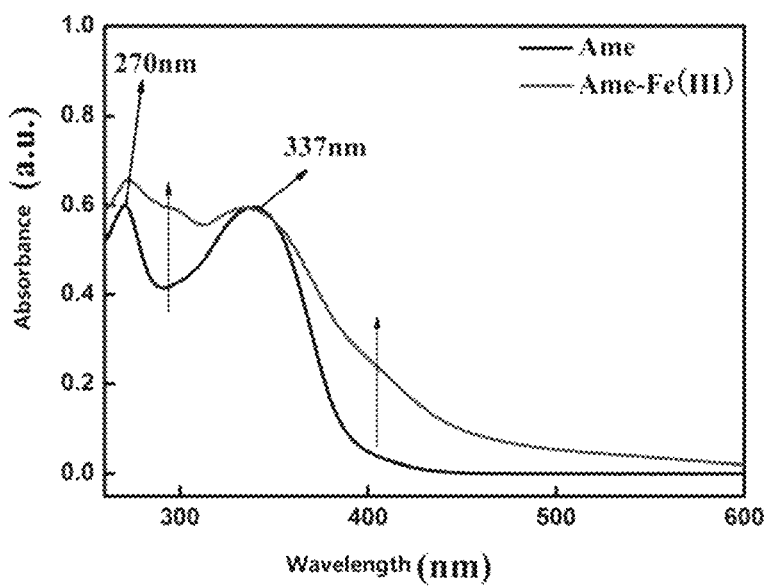
FIG. 2 is a diagram showing UV-vis spectra of an Ame and an Ame-Fe complex.

The UV-vis spectra of the Ame and the Ame-Fe complex are shown in FIG. 2. The Ame has two characteristic absorption peaks at 337 nm (band I) and 270 nm (band II), which are the characteristic absorptions of the flavonoid compounds. Band I and band II correspond to the UV absorptions of the cinnamyl system and the benzoyl system, respectively, which are caused by the π-π* transition. The Ame-Fe complex produces an absorption platform between 375-450 nm, which is caused by the red shift of the band I, indicating that the cinnamyl system participates in the coordination. Although the position of the band II does not change significantly, the absorption intensity decreases relatively, and the absorption peak at 250-330 nm is increased. These phenomena indicate that the carbonyl group of the cinnamyl system and the benzoyl system participates in the coordination. After the coordination, the conjugated system increases, the energy required for the electronic transition decreases, and the π-π* transition is more likely to occur, so the band I is red-shifted. However, 4-C=O is more prone to trigger π-π* transition, so a new peak is generated at 298 nm. It can be speculated that the site where Fe$^{3+}$ forms a complex with Ame is 5-OH, 4-C=O, 5″-OH, and 4″-C=O.

In a positive ion mode, the mass spectrometric analysis of the Ame and Ame-Fe complex were carried out, and the ion structure corresponding to the molecular ion peaks on the spectrum was obtained by simulation according to mass spectra, thus the structure of the Ame-Fe was speculated.

Figure 3:
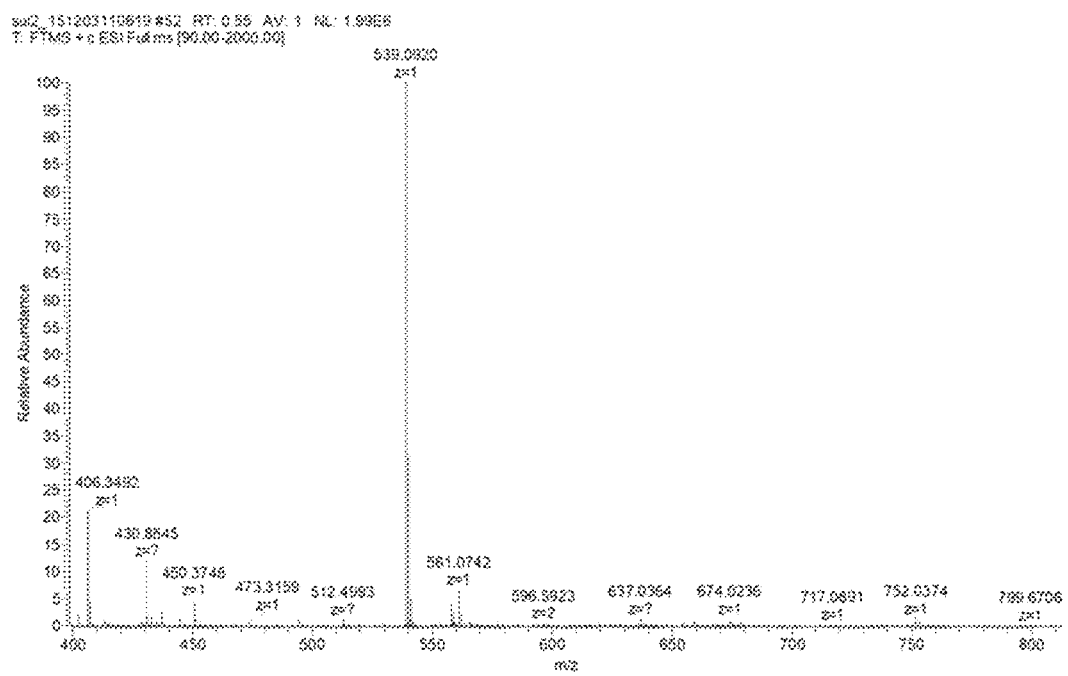
FIG. 3 is a mass spectrum of an Ame.
Figure 4:
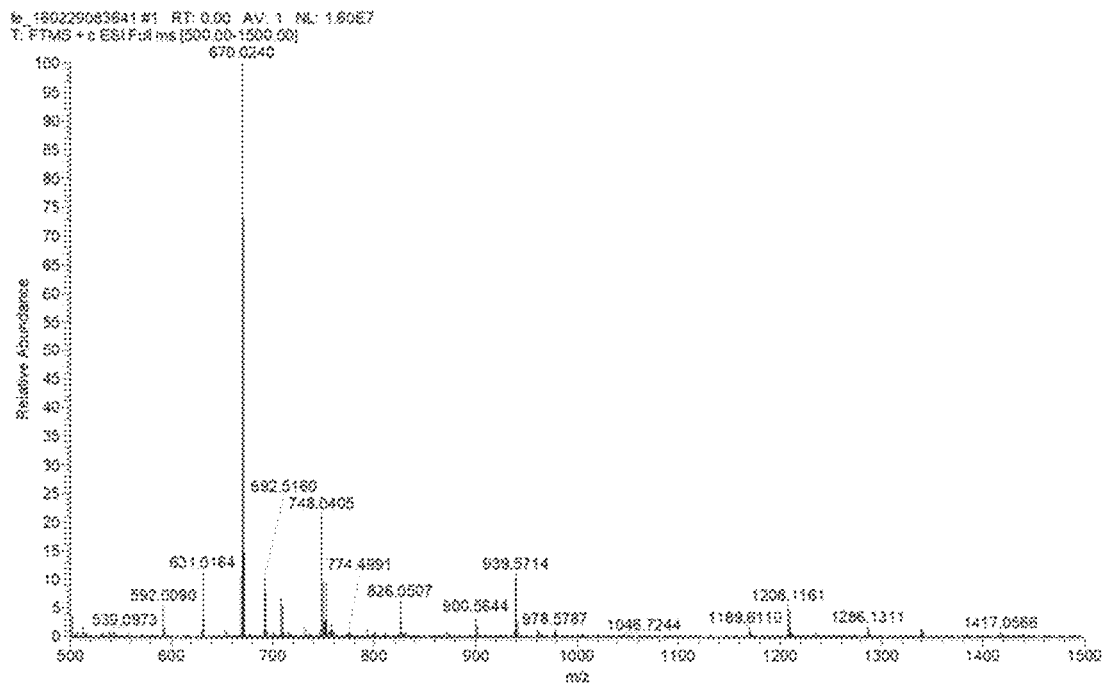
FIG. 4A is a mass spectrum of an Ame-Fe complex.
FIG. 4B is an isotope mass spectrum of an Ame-Fe complex.
FIG. 4C is a mass spectrum showing a possible elemental composition of a quasi-molecule ion peak m/z 670.0240.
FIG. 4D is a simulated mass spectrum.
Figure 4B:
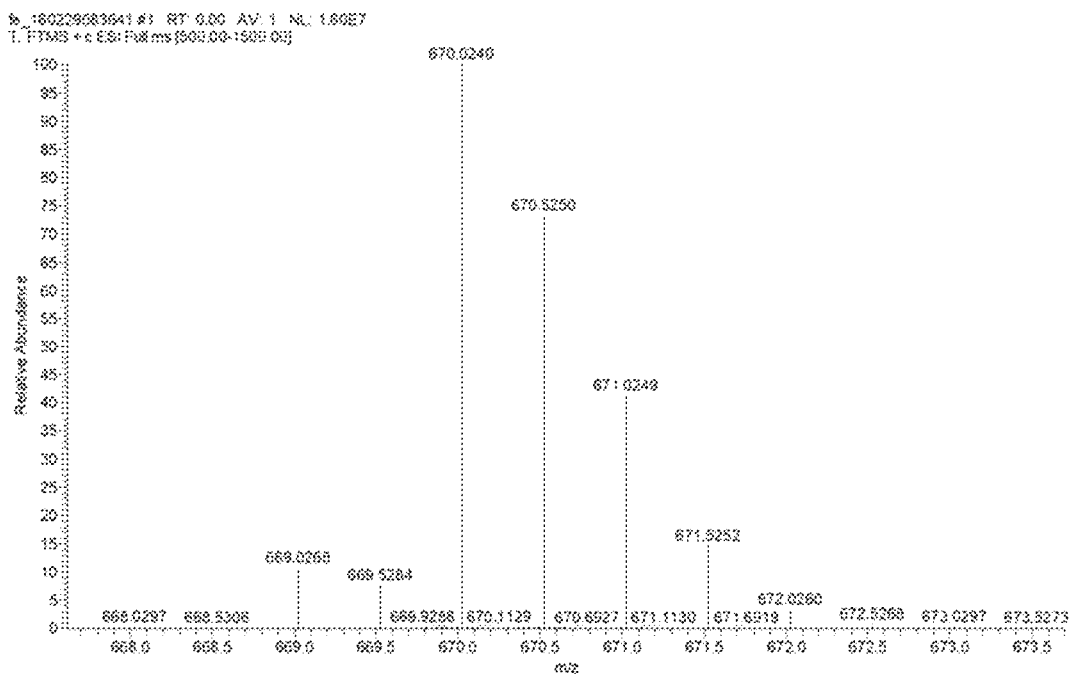
Figure 4C:
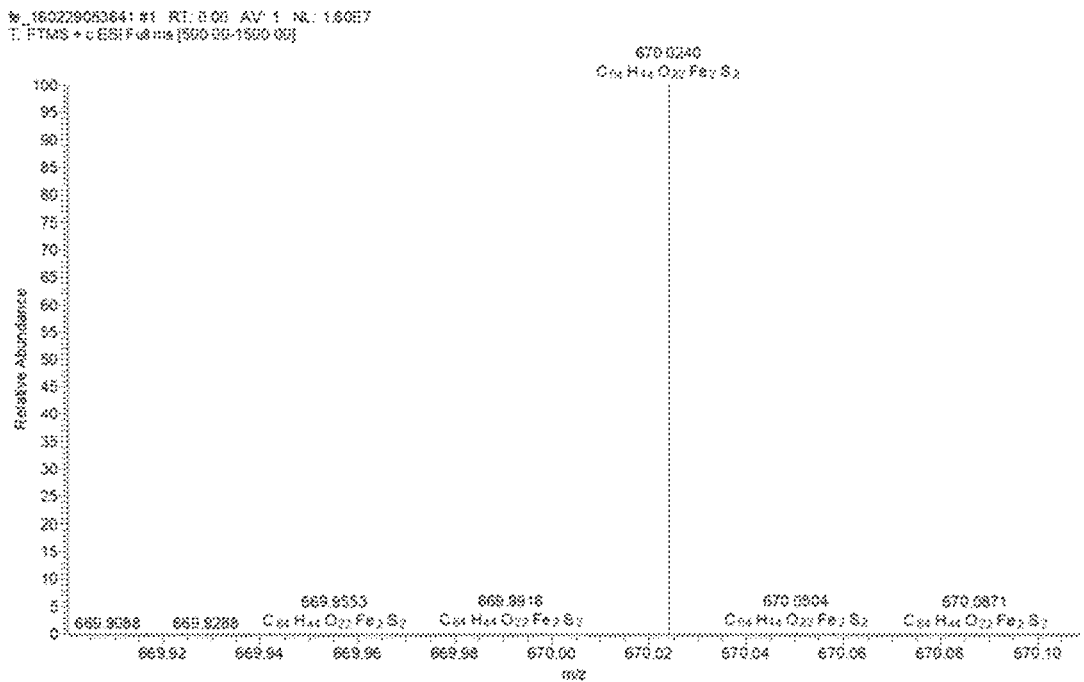
Figure 4D:
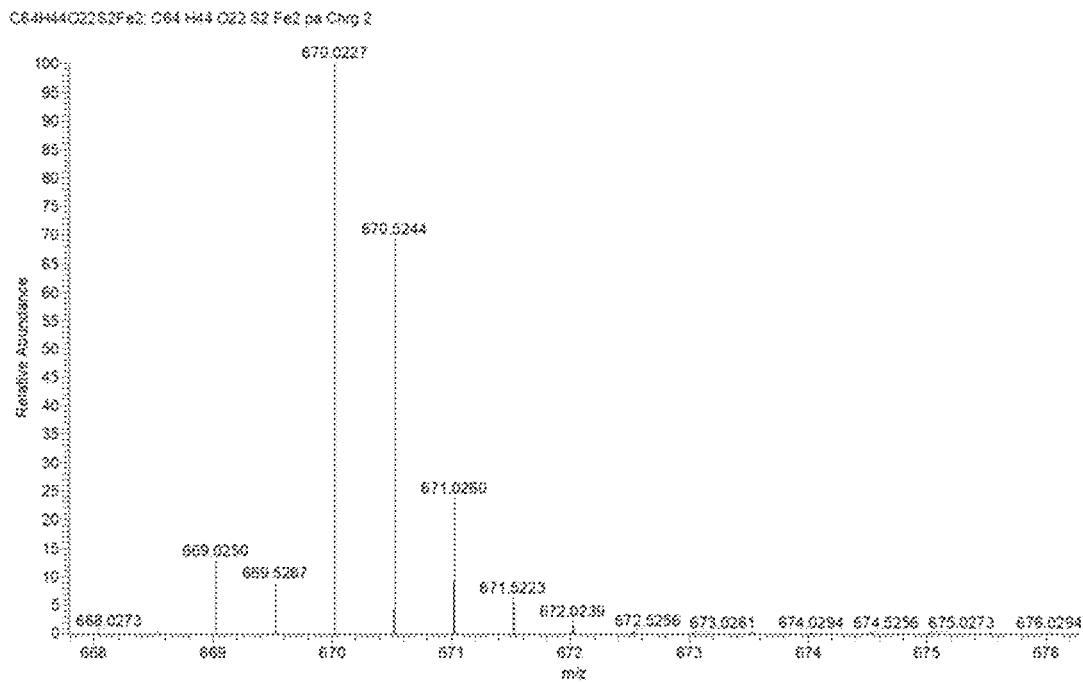

FIG. 3 is a mass spectrum of the Ame in the positive ion mode with the quasi-molecule ion peak m/z 539.0920 belonging to [Ame+H]$^+$. FIG. 4A is a mass spectrum of the Ame-Fe complex, which shows that the quasi-molecule ion peak of the Ame-Fe complex is an ion peak m/z 670.0240 with two positive charges. From its isotope mass spectrum (FIG. 4B), it can be seen that the isotope peaks of the quasi-molecule ion peaks are mainly m/z 669.0268, m/z 669.5284, m/z 670.5250, m/z 671.0249, m/z 671.5252, and m/z 672.0260, and the molecular weights of adjacent ion peaks differ by 0.5016, 0.4956, 0.5010, 0.4999, 0.5003, and 0.5008, respectively, confirming that the quasi-molecule ion peak carries two positive charges. It can be seen from the IR spectrum and the UV-vis spectrum that the coordination sites where the Ame forms a complex with Fe$^{3+}$ are 5-OH, 4-C=O, 5″-OH and 4″-C=O. Since the solvent for recrystallization and dissolution of the complex is DMSO, DMSO contains an oxygen atom and a sulfur atom, which has a strong coordination ability and is difficult to ionize, the complex may contain DMSO, thus speculating that the quasi-molecule ion peak m/z 670.0240 belongs to [Fe$_2$(Ame-2H)$_2$(DMSO)$_2$]$^{2+}$. The elemental composition is C$_{64}$H$_{44}$O$_{22}$Fe$_2$S$_2$, which is consistent with the possible elemental composition of the quasi-molecule ion peak m/z 670.0240 (FIG. 4C). Moreover, [Fe$_2$(Ame-2H)$_2$(DMSO)$_2$]$^{2+}$ was simulated by mass spectrometry simulation software to obtain the simulated mass spectrum as shown in FIG. 4D. It can be seen from the figure that the isotope ion peaks of [Fe$_2$(Ame-2H)$_2$(DMSO)$_2$]$^{2+}$ are m/z 669.0250, m/z 669.5267, m/z 670.0227, m/z 670.5244, m/z 671.0260, m/z 671.5223, and m/z 672.0239, respectively, which are highly matched to the isotope mass spectrum peak of the quasi-molecule ion peak m/z 670.0240. Therefore, it can be confirmed that the ion corresponding to the molecular ion peak m/z 670.0227 is [Fe$_2$(Ame-2H)$_2$(DMSO)$_2$]$^{2+}$. In summary, Ame and Fe$^{3+}$ form a complex in a ratio of 2:2. The coordination sites where the Ame forms a complex with Fe$^{3+}$ are confirmed to be 5-OH, 4-C=O, 5″-OH and 4″-C=O by IR spectrum and UV-vis spectrum. Therefore, the most likely structural formula of [Fe$_2$(Ame-2H)$_2$(DMSO)$_2$]$^{2+}$ is as follows:

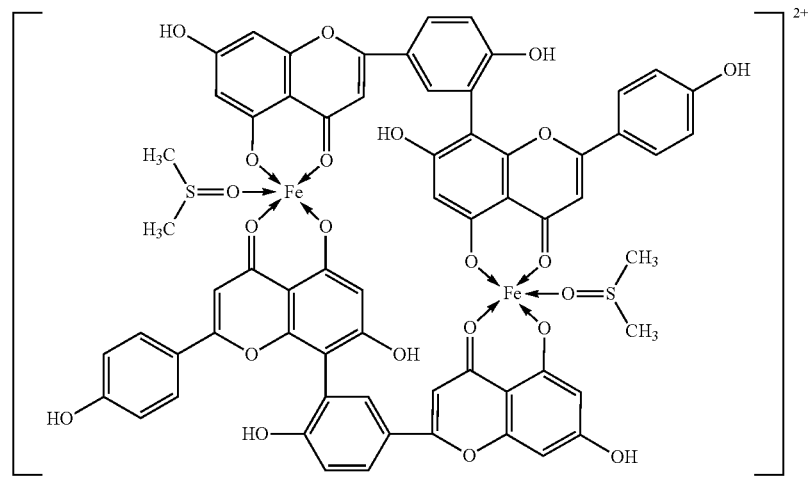

In addition, since the metal salt in the experiment is a nitrate or a hydrochloride, the complex contains nitrate or chloride ions. Therefore, the structural formula of the Ame-Fe complex is as follows:

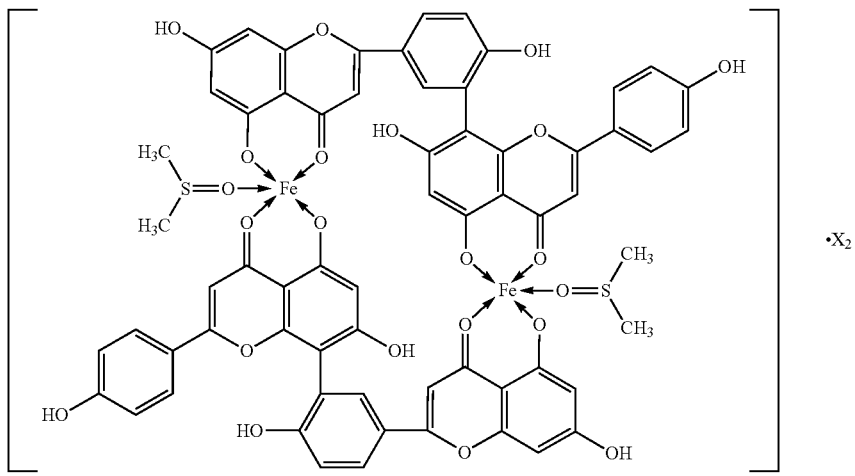

X is $NO_3^-$ or $Cl^-$.

Embodiment 10

The antitumor activity of Ame and Ame-Fe complex were studied by MTT method with the following process:

(1) the HepG2 and HeLa cell suspensions were inoculated into 96-well culture plates, 100 μL was added for each well, ($1\times10^5$/mL), and then cultured in a 5% $CO_2$ incubator at 37° C. for 24 h;

(2) after culturing for 24 h, the supernatant was discarded, 100 μL of pre-diluted sample was added, 10 replicate wells were set for each concentration, and then incubated in the 5% $CO_2$ incubator for 24 h; meanwhile, control wells (DMSO, cell suspension, MTT), and blank wells (medium, DMSO, MTT) were set;

(3) After culturing for 36 h, the supernatant was discarded, 100 μL of DMEM medium containing MTT (5 mg/mL) were added, and then continuously cultured for 4 h;

(4) After 4 h, the supernatant was carefully scavenged, 200 μL of DMSO was added to each well, adequate shaking was performed for 15 min in a constant temperature oscillator, the absorbance was measured at 595 nm by a microplate reader, the inhibition rates of the sample to HepG2 and HeLa cells were calculated by OD value, and the half-inhibitory concentration $IC_{50}$ value was calculated by using the modified Karber formula.

$$IR = 1 - \frac{OD_1}{OD_0} \quad \text{(Formula 1)}$$

$$lgIC_{50} = Xm - I(P - (3 - Pm - Pn)/4) \quad \text{(Formula 2)}$$

Where, IR is the inhibition rate, $OD_0$ is the absorbance of the control group, $OD_1$ is the absorbance of the sample group, Xm is 1 g (the maximum dose), I is 1 g (the maximum dose/adjacent dose), P is the sum of positive reaction rates, Pm is the maximum positive reaction rate, and Pn is the minimum positive reaction rate.

Figure 5:
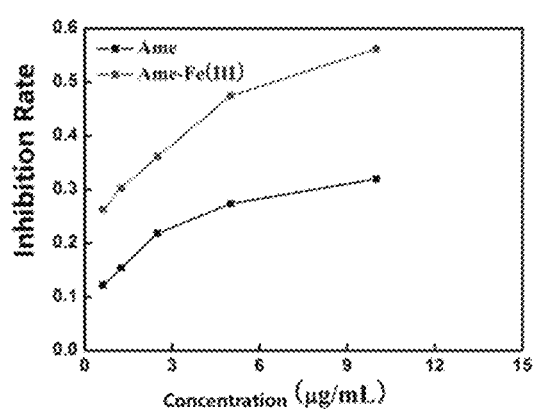
FIG. 5 is a diagram showing results of inhibition effects of an Ame and an Ame-Fe complex on HegG2 cells.
Figure 6:
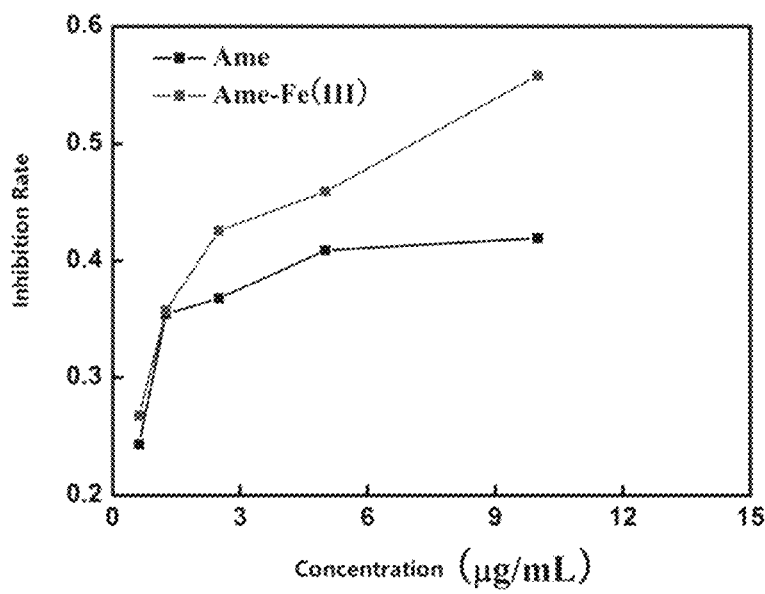
FIG. 6 is a diagram showing results of inhibition effects of an Ame and an Ame-Fe complex on HeLa cells.
Figure 7:
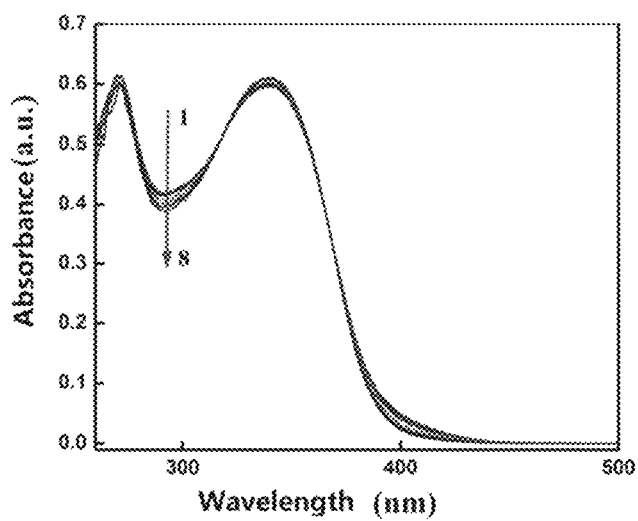
FIG. 7 is a diagram showing a result of an effect of fDNA on the UV-vis spectrum of the Ame.
Figure 8:
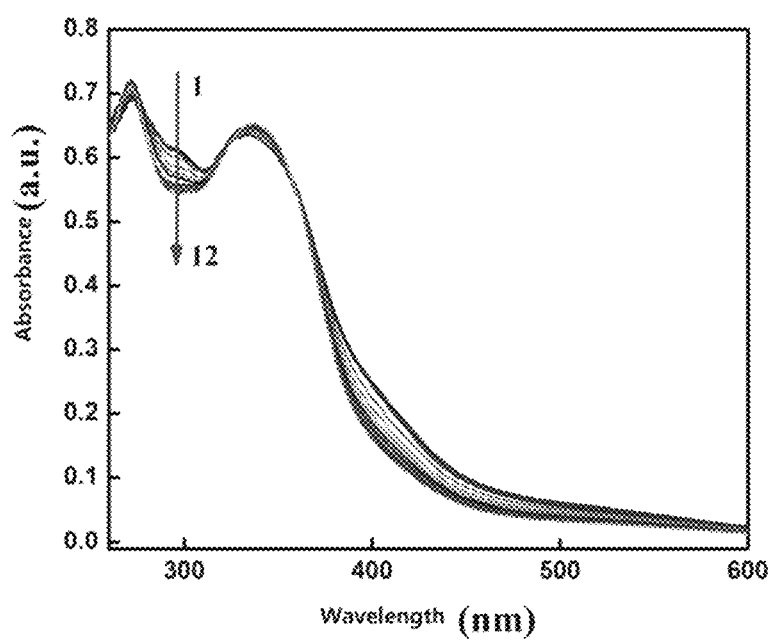
FIG. 8 is a diagram showing a result of an effect of fDNA on the UV-vis spectrum of the Ame-Fe complex.
Figure 9:
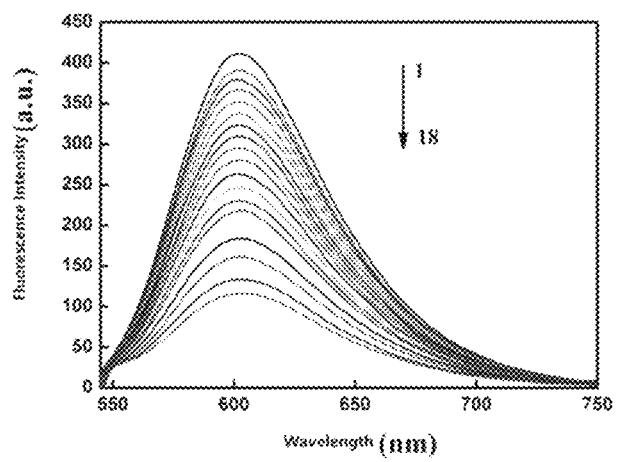
FIG. 9 is a diagram showing a result of an effect of an Ame on a fluorescence emission spectrum of an fDNA-EB system.
Figure 10:
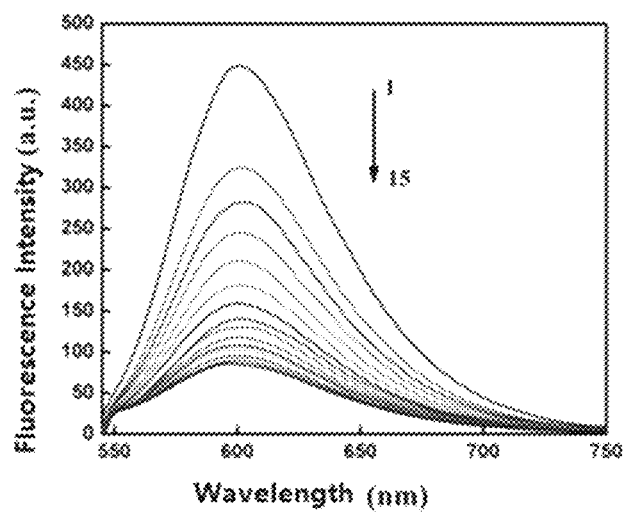
FIG. 10 is a diagram showing a result of an effect of an Ame-Fe complex on a fluorescence emission spectrum of an fDNA-EB system.
Figure 11:
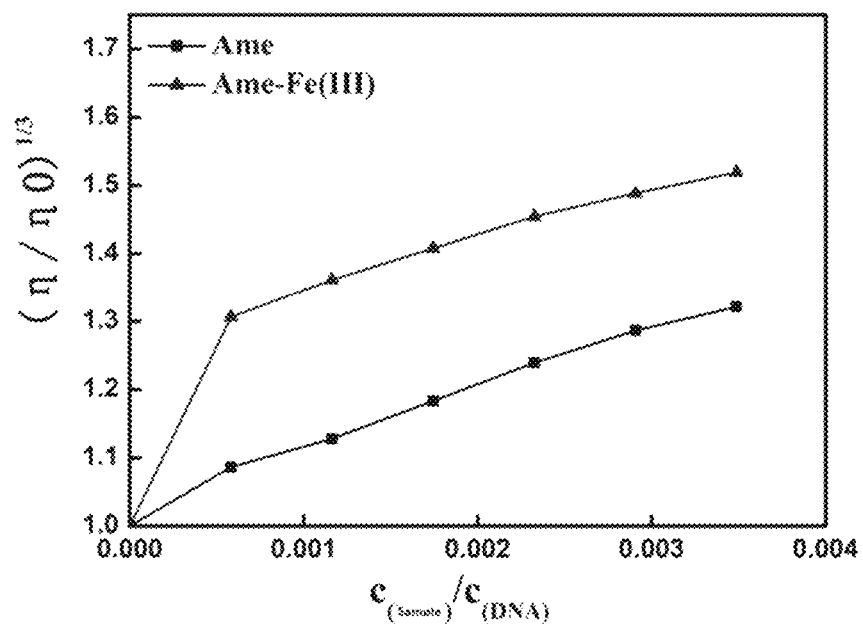
FIG. 11 is a diagram showing results of effects of an Ame and an Ame-Fe complex on a viscosity of an fDNA solution.
Figure 12:
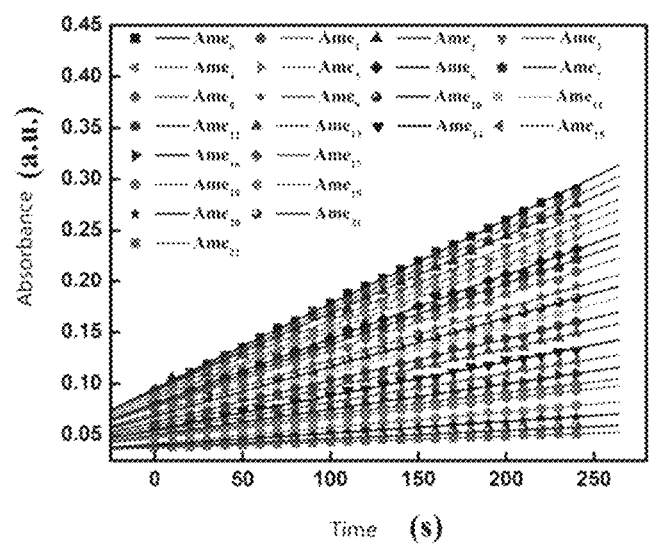
FIG. 12 is a diagram showing a result of an effect of an Ame on an auto-oxidation rate of pyrogallol.
Figure 13:
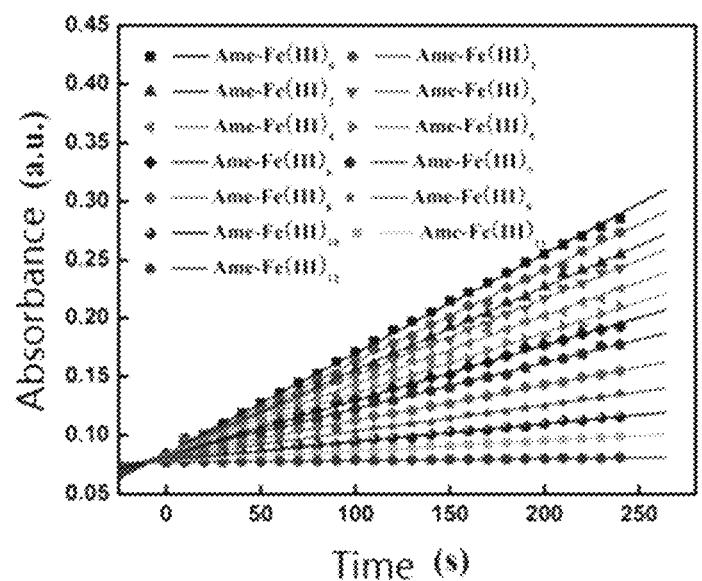
FIG. 13 is a diagram showing a result of an effect of an Ame-Fe complex on an auto-oxidation rate of pyrogallol.
Figure 14:
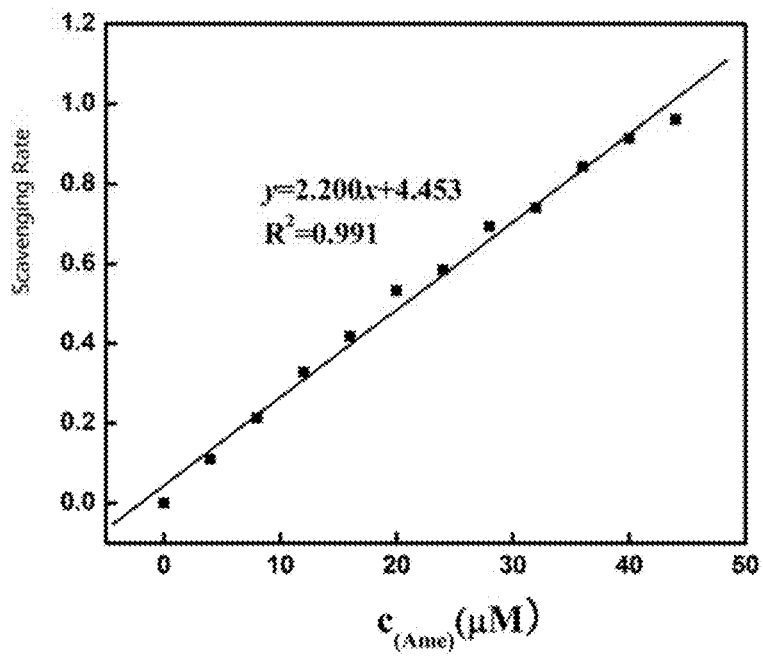
FIG. 14 is a diagram showing a result of an $ABTS^+$. free radical scavenging ability of an Ame.
Figure 15:
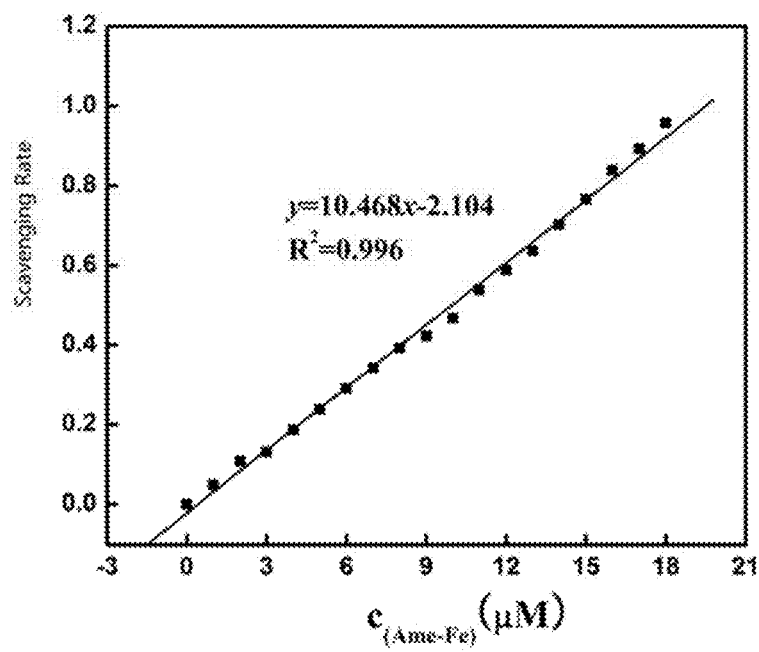
FIG. 15 is a diagram showing a result of an $ABTS^+$. free radical scavenging ability of an Ame-Fe complex.

The results are shown in FIGS. 5-6. It is found that Ame-Fe complex can effectively inhibit the growth of the hepatoma cells (HepG2) and the cervical cancer cells (HeLa), $IC_{50}$ values thereof are 3.144 and 2.922 μmol·$L^{-1}$, respectively, which is smaller than the $IC_{50}$ values of the Ame (The $IC_{50}$ values of Ame are 13.633 and 8.040 μmol·$L^{-1}$, respectively), indicating that the Ame-Fe complex has better antitumor activity than the Ame. UV-vis spectroscopy, fluorescence spectroscopy and viscosity method are used to study the interaction between the Ame/Ame-Fe complex and herring sperm DNA (fDNA) to further reveal the mechanism of antitumor activity, the obtained spectra are shown in FIGS. 7-11. The results show that the interaction between the Ame/Ame-Fe complex and the fDNA is in the intercalation manner, and the interaction between the complex and the fDNA is stronger than that between the Ame and the fDNA. Thereby, it can be speculated that the mechanism of antitumor activity of the Ame and its complex may be that Ame or the complex thereof enters the interior of the cell and intercalates with the DNA strand to cause apoptosis. Since the interaction of the complex with DNA is stronger than of the Ame, the antitumor activity thereof is also stronger than of the Ame.

Embodiment 11

The free radical scavenging abilities of the Ame and the Ame-Fe complex were studied by pyrogallol auto-oxidation method and ABTS method with the following steps:

(1) Pyrogallol Auto-Oxidation Method

Determination of auto-oxidation rate $V_0$ of pyrogallol: 2 mL Tris-HCl buffer (pH=8.20) was added to a 10 mL sample tube at 25° C., 100 μL, DMSO was added as a control, after adding 0.8 mL distilled water, 0.2 mL pyrogallol solution having a concentration of 2 mmol·$L^{-1}$ was added, the mixture was poured into a cuvette after mixing uniformly, the absorbance at 322 nm was measured with pure water as a blank, the A value was recorded every 10 s for a total of 4 min, linear regression was performed with t as the abscissa, and A as the ordinate, straight line slope thereof is $V_0$, and the measurement was performed for three times to obtain an average value.

Determination of auto-oxidation rate $V_1$ of pyrogallol after adding sample: 2 mL Tris-HCl buffer (pH=8.2) was added to a 10 mL sample tube at 25° C., 100 μL samples of various concentrations that were dissolved in DMSO were added, after adding 0.8 mL distilled water, 0.2 mL pyrogallol solution having a concentration of 2 mmol·$L^{-1}$ was added, the mixture was poured into a cuvette after mixing uniformly, the absorbance at 322 nm was measured with double distilled water as a blank, the A value was recorded every 10 s for a total of 4 min, linear regression was performed with t as the abscissa, and A as the ordinate, straight line slope thereof is $V_1$, and the measurement was performed for three times to obtain an average value. The free radical scavenging rate was calculated according to Formula 3.

$$SR(\%) = (1 - v_1/v_0) \times 1.00\%$$ (Formula 3)

(2) ABTS Method

Determination of ABTS$^+$. free radical ion scavenging ability of the blank sample: at 25° C., 2.9 mL ABTS$^+$. free radical ion working solution was added into a 10 mL sample tube, 100 μL DMSO was added, after reacting for 5 min, the UV-vis spectrum was measured, and the absorption intensity $A_0$ at 730 nm was recorded.

Determination of ABTS$^+$. free radical ion scavenging ability of the samples: at 25° C., 2.9 mL ABTS$^+$. free radical ion working solution was added into a 10 mL sample tube, 100 μL samples of different concentrations that were dissolved in DMSO were added, after reacting for 5 min, the UV-vis spectrum was measured, and the absorption intensity $A_1$ at 730 nm was recorded, and the ABTS$^+$. free radical ion scavenging rate was calculated according to Formula 4.

$$SR(\%) = (1 - A_1/A_0) \times 1.00\%$$ (Formula 4)

As shown in FIGS. 12-15, the results of pyrogallol auto-oxidation method show that the IC$_{50}$ of the Ame and the Ame-Fe complex to scavenge O$_2^-$. free radical are 23.273 μmol·L$^{-1}$ and 3.123 μmol·L$^{-1}$, and it can be found that the O$_2^-$. free radical scavenging ability of the Ame-Fe complex is significantly stronger than that of the Ame.

The ABTS$^+$. free radical scavenging abilities of the Ame and the Ame-Fe complex are concentration dependent. Within a certain range, the scavenging rate is linear with the concentration. The curve of the scavenging rate and the concentration (c) is plotted in the present invention to obtain a corresponding linear equation, and the maximum half-inhibitory concentration (IC$_{50}$ value) is calculated. The IC$_{50}$ values of the Ame and the Ame-Fe complex for scavenging ABTS$^+$. free radicals are 20.703 and 4.977 μmol·L$^{-1}$, respectively. It can be seen that the ABTS$^+$. free radical scavenging ability of the Ame-Fe complex is significantly stronger than that of the Ame.

What is claimed is:

1. A biflavone-iron complex, comprising the following structural formula:

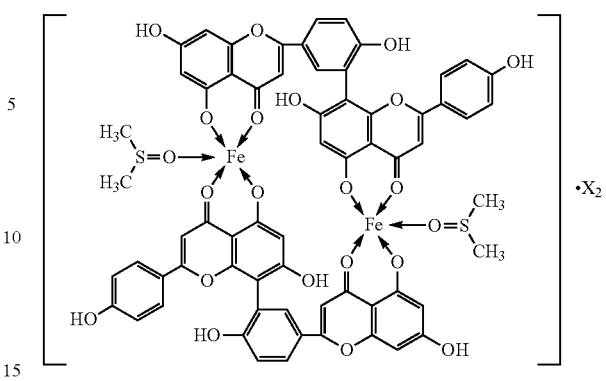

wherein, X is NO$_3^-$ or Cl$^-$.

2. A method of preparing the biflavone-iron complex of claim 1, comprising:
   dissolving a ferric salt in an alcohol and adding into a biflavone dissolved in the alcohol to obtain a mixed solution; heating and stirring the mixed solution, and reacting the mixed solution for 2-5 h to form a precipitate at a pH controlled to be 5-7;
   filtering the precipitate from the mixed solution, washing the precipitate with alcohol and water, and then recrystallizing using dimethyl sulfoxide as a solvent to obtain a recrystallized precipitate, and
   drying the recrystallized precipitate to obtain the biflavone-iron complex;
   wherein, the biflavonoid is amentoflavone, and the iron salt is ferric nitrate or ferric chloride.

3. The method of preparing the biflavone-iron complex of claim 2, wherein the pH is adjusted with an alkali alcohol solution, and an alkali used in the alkali alcohol solution is selected from the group consisting of sodium hydroxide, potassium hydroxide, ammonia water, sodium ethoxide, and sodium methoxide.

4. The method of preparing the biflavone-iron complex of claim 2, wherein a reaction temperature is 30-50° C., and a reaction time is 2-5 hours.

5. The method of preparing the biflavone-iron complex of claim 2, wherein a molar ratio of the biflavone to ferric ion in the mixed solution is 2-2.5:1.

6. The method of preparing the biflavone-iron complex of claim 2, wherein the solvent used in the recrystallizing is dimethyl sulfoxide, and the drying is a freeze-drying, or a low temperature vacuum-drying.

* * * * *